United States Patent
Patel et al.

(10) Patent No.: US 6,819,951 B2
(45) Date of Patent: Nov. 16, 2004

(54) PERIPHERALLY INSERTED CENTRAL CATHETER WITH CONTINUOUS CENTRAL VENOUS OXIMETRY AND PROXIMAL HIGH FLOW PORT

(75) Inventors: Bhavesh Patel, Scottsdale, AZ (US); Corinna Dauenhauer, Scottsdale, AZ (US); Dipakkumar M. Patel, Edmonton (CA)

(73) Assignee: Mayo Foundation for Medical Education and Research, Rochester, MN (US)

( * ) Notice: Subject to any disclaimer, the term of this patent is extended or adjusted under 35 U.S.C. 154(b) by 26 days.

(21) Appl. No.: 10/253,745

(22) Filed: Sep. 24, 2002

(65) Prior Publication Data

US 2004/0059211 A1 Mar. 25, 2004

(51) Int. Cl.⁷ .................................................. A61B 5/00
(52) U.S. Cl. ....................................... 600/339; 600/342
(58) Field of Search ................................ 600/310, 322, 600/323, 324, 325, 327, 337, 339, 341, 342, 481, 485, 486, 487

(56) References Cited

U.S. PATENT DOCUMENTS

| | | | |
|---|---|---|---|
| 3,847,483 A | * | 11/1974 | Shaw et al. .................... 356/41 |
| 4,623,248 A | * | 11/1986 | Sperinde ..................... 600/342 |
| 4,651,741 A | | 3/1987 | Passafaro |
| 4,711,522 A | | 12/1987 | McCartney |
| 4,718,423 A | | 1/1988 | Willis et al. |
| 4,960,409 A | | 10/1990 | Catalano |
| 5,007,704 A | | 4/1991 | McCartney |
| 5,160,325 A | | 11/1992 | Nichols et al. |
| 5,196,004 A | | 3/1993 | Sinofsky |
| 5,275,169 A | | 1/1994 | Afromowitz et al. |
| 5,315,995 A | | 5/1994 | Rivers |
| 5,435,308 A | * | 7/1995 | Gallup et al. ............... 600/342 |
| 5,624,704 A | | 4/1997 | Darouiche et al. |
| 5,673,694 A | | 10/1997 | Rivers |
| 5,715,816 A | | 2/1998 | Mainiero et al. |
| 5,752,941 A | | 5/1998 | Romano' et al. |
| 5,754,716 A | | 5/1998 | Kim et al. |
| 5,810,738 A | | 9/1998 | Thomas, II |
| 5,810,789 A | | 9/1998 | Powers et al. |
| 5,902,283 A | | 5/1999 | Darouiche et al. |
| 5,921,965 A | | 7/1999 | Blei |
| 6,036,654 A | | 3/2000 | Quinn et al. |
| 6,299,583 B1 | | 10/2001 | Eggers et al. |

OTHER PUBLICATIONS

Central Venous Pressure Measurements: Peripherally Inserted Catheters Versus Centrally Intersted Catheters, Crit Care Med 2000, vol. 28, No. 12, Black MD, et al.
www.obex.co.nz/CookCC.htm, Cook Critical Care, p. 1–5.

* cited by examiner

Primary Examiner—Eric F. Winakur
(74) Attorney, Agent, or Firm—Quarles & Brady LLP

(57) ABSTRACT

A peripherally inserted central catheter includes three lumens that communicate with its proximal end. A large lumen terminates short of the distal end of the catheter and is used for the infusion of fluids into the venous system. A second lumen terminates at the distal end and is suitable for measuring blood pressure in the central venous system and infusion of fluids into the central venous system. The third lumen houses a pair of optical fibers which form part of a central venous oxygen saturation ($S_vO_2$) monitoring system.

10 Claims, 4 Drawing Sheets

PERIPHERALLY INSERTED CENTRAL CATHETER WITH CONTINUOUS CENTRAL VENOUS OXIMETRY AND PROXIMAL HIGH FLOW PORT

BACKGROUND OF THE INVENTION

The field of the invention is catheters, and in particular catheters inserted into the central venous system.

Oxygen is essential to human life. An immediate cascade of pathologic processes is triggered in response to a decrease in oxygen delivery. Since oxygen is not stored in sufficient quantities in the body, inadequate oxygen transport to the cells for even very brief periods of time can result in organ failure and death. Thus our ability to monitor and increase oxygen delivery to the body is essential to preventing and reversing organ dysfunction (such as heart, kidney and liver failure or coma) and death. The goal is to balance oxygen supply with tissue oxygen demand.

In an effort to properly balance oxygen supply and demand a number of measurements are commonly made. Current monitoring techniques include continuous electrocardiographic monitoring, measurement of blood pressure, measurement of skin temperature and capillary refill. These noninvasive techniques provide little information regarding hemodynamic status and/or oxygen delivery to the brain or body (tissue).

Mixed venous oxygen saturation ($SvO_2$) is the amount of oxygen in blood taken from a vessel coming from the right side of the heart going into the lungs. This reflects the amount of oxygen being delivered to the tissues. When oxygen delivery to the tissues is inadequate, the $SvO_2$ is low. When oxygen delivery to the tissues is adequate, the $SvO_2$ is normal or high. This is the physiological basis for using $SvO_2$ as the earliest indicator of response to therapy during patient treatment.

Ideally, $SvO_2$ is drawn from a pulmonary artery catheter which is approximately 100 centimeters long and is placed into a vein that accesses the right side of the heart and then into the pulmonary artery. However, placement of a pulmonary artery catheter is extremely difficult and can be impractical during cardiac arrest and severe shock due to low blood pressure and may actually increase patient mortality.

The central venous system avoids traversing the heart and can be more easily accessed. Thus, a number of studies have supported the substitution of central venous (right atrial or superior vena cava) oxygen saturation ($ScvO_2$) for pulmonary artery blood oxygen saturation ($SvO_2$). The central venous blood can be obtained much more easily than blood from the pulmonary artery because the heart does not need to be traversed.

Central venous measurement of oxygen saturation ($SvO_2$) is currently achieved by puncture of the central venous circulation (CVC) system (i.e., internal jugular vein, subclavian vein or femoral vein) and insertion of an intravascular catheter device such as that disclosed in U.S. Pat. No. 5,673,694. Such CVC catheters employ fiber optics to measure $SvO_2$ as described, for example, in U.S. Pat. Nos. 5,754,716 and 4,711,522. They are relatively short (i.e., less than 30 cm in length) and inflexible devices which can remain in place for only a short time (e.g., generally less than 7 days).

The use of CVC catheters to measure oxygen saturation and blood pressure from the superior vena cava or right atrium has a number of drawbacks. These CVC catheter insertions are known to be associated with complications of lung puncture (pneumothorax), major hemorrhage, neck hematoma, carotid artery puncture, cardiac dysrhythmias and infection. In addition, because they can remain in place for only a short time, repeated insertions are necessary when monitoring is required over a long time period.

Peripherally inserted central venous catheters have been available for many years to administer fluids such as parenteral nutrition, chemotherapy, vasopressor (adrenalin like medications), antibiotics and other hypertonic/caustic solutions. These catheters are also used for blood draws. These catheters are inserted into peripheral veins (generally the antecubital, basilic or cephalic veins) and advanced into the central (deep) venous system with the tip ideally positioned in the superior vena cava or right atrium thus allowing for dilution of infused fluids.

The use of such peripheral catheters avoids the complications associated with the direct puncture of the central venous circulation system and they can remain in place for extended periods of time. However, due to their longer length, smaller diameter and greater flexibility, peripheral catheters have not been used for rapid infusion measurement of central venous blood pressure or continuous central venous oximetry.

SUMMARY OF THE INVENTION

The present invention is a multilumen catheter which can be inserted via a superficial (peripheral) vein into the central venous system for drug infusion, phlebotomy, rapid fluid infusion, hemodynamic pressure monitoring and central venous oxygen saturation monitoring. More specifically, the catheter includes a sheath having a length and diameter suitable for extending from a peripheral vein insertion point to the superior vena cava of the patient and having two lumens formed therein which extend from its proximal to its distal ends. A pair of optical fiber cables extend through one lumen and connect to an oxygen saturation measurement instrument at the proximal end, and a medical instrument such as a blood pressure monitor connects to the proximal end of the other lumen.

One object of the invention is to monitor central venous oxygen saturation using a peripherally inserted catheter. The peripheral insertion results in the need for a substantially longer and more flexible sheath while at the same time providing protection for the delicate optical fibers used by the oxygen saturation measurement instrument.

Another object is to provide a peripherally inserted catheter which enables simultaneous measurement of central venous blood pressure and oxygen saturation. One lumen houses the optical fibers needed for oxygen saturation measurement, and the other lumen may be employed to monitor blood pressure in the central venous system.

Another aspect of the invention is the addition of a third lumen in the sheath which has a size sufficient to rapidly infuse fluids. Flow rate is increased by terminating the third lumen at a port in the sheath located at a point intermediate its ends. The port is located with respect to the distal end of the sheath such that fluid flows into or proximal to the subclavian vein when the distal end of the sheath is positioned in the superior vena cava.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
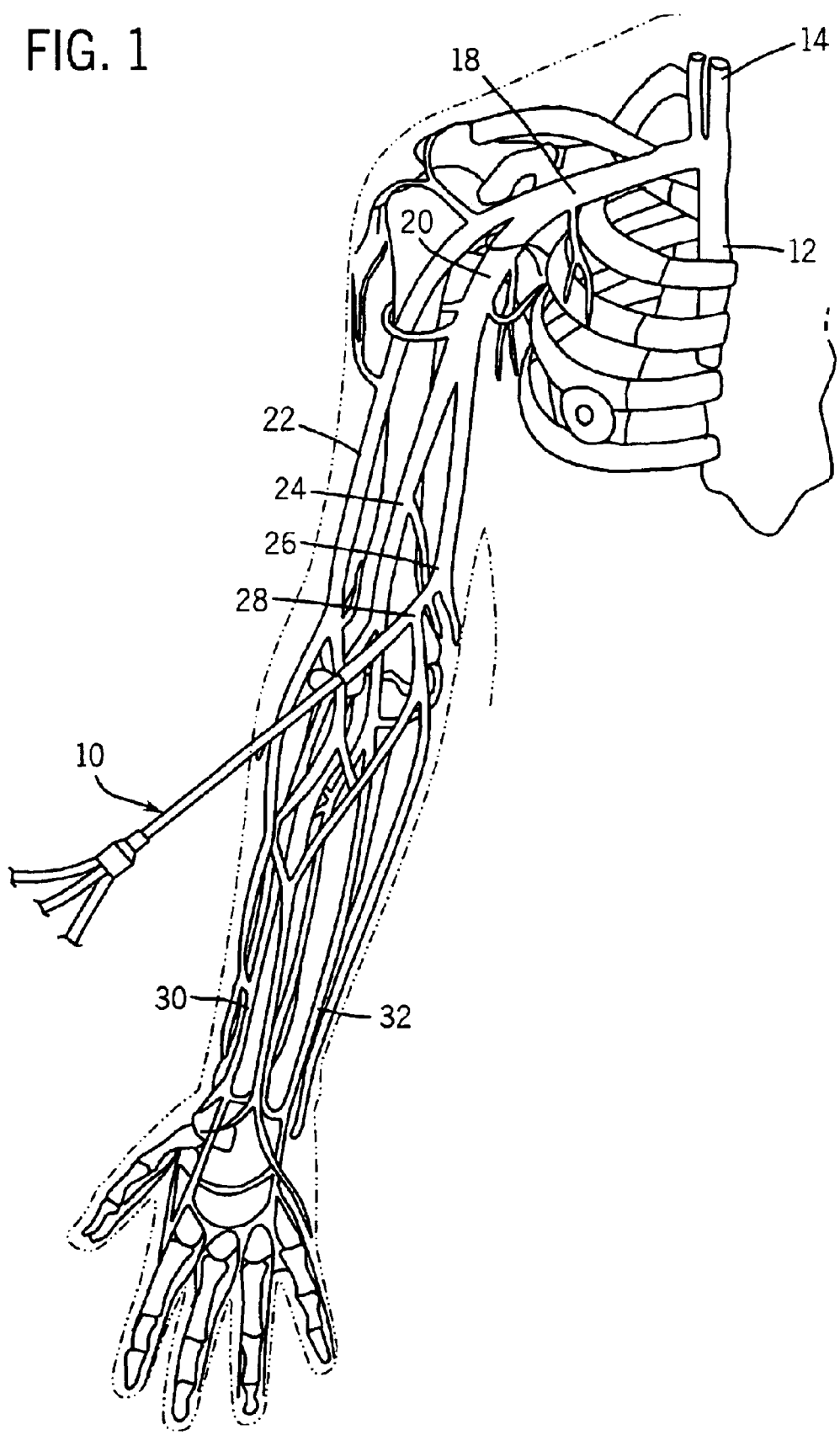
FIG. 1 is a partial pictorial view of the venous system of a human subject.

Referring particularly to FIG. 1, the catheter 10 of the present invention is inserted into a superficial, or peripheral vein of a patient. The central venous system is comprised of the superior vena cava 12 which extends downward into the right atrium of the heart (not shown in the drawings) and a set of veins which connect to it. These central venous system veins include the internal jugular vein 14, the subclavian vein 18, the axillary vein 20 and brachial vein 24.

These central venous system veins lie deep beneath subcutaneous tissue and accompany large arteries. They are supplied with blood from a network of smaller, peripheral veins that extend throughout the limb of the patient and are located just under the skin (hence the term "superficial" veins). In the arm shown in FIG. 1, these peripheral veins include the cephalic vein 22, the basilic vein 26 and cubital vein 28 in the upper arm as well as the radial vein 30 and ulnar vein 32 in the lower arm. Some of these peripheral veins are better than others for insertion of a catheter. Unlike the cephalic vein, the basilic vein does not collapse or kink with flexion of the deltoid and pectoral muscles, and is of larger caliber, providing a more favorable vein-to-catheter ratio. Avoiding distal and intracubital placement improves patient perception of mobility for activities of daily living and averts catheter "kinking" with arm flexion.

There are two requirements of a peripherally inserted central catheter which distinguish it from a central venous circulation (CVC) catheter. First, it is much longer. The distance from the superior vena cava 12 from a typical subclavian insertion point is only 15 cm, whereas the distance from a peripheral insertion point such as cephalic vein, basilic vein or cubital vein is from 40 to 60 cm.

The second major distinction is that the peripherally inserted catheter must have more flexibility than a CVC catheter. The CVC catheter has a relatively short, straight run to the superior vena cava, whereas the peripheral catheter has a longer, more tortuous path. In addition, the peripheral veins are smaller in size and not as rigidly anchored in place. Flexibility is required, therefore, in order to easily wind the peripheral catheter through the smaller, compliant peripheral veins.

Figure 2:
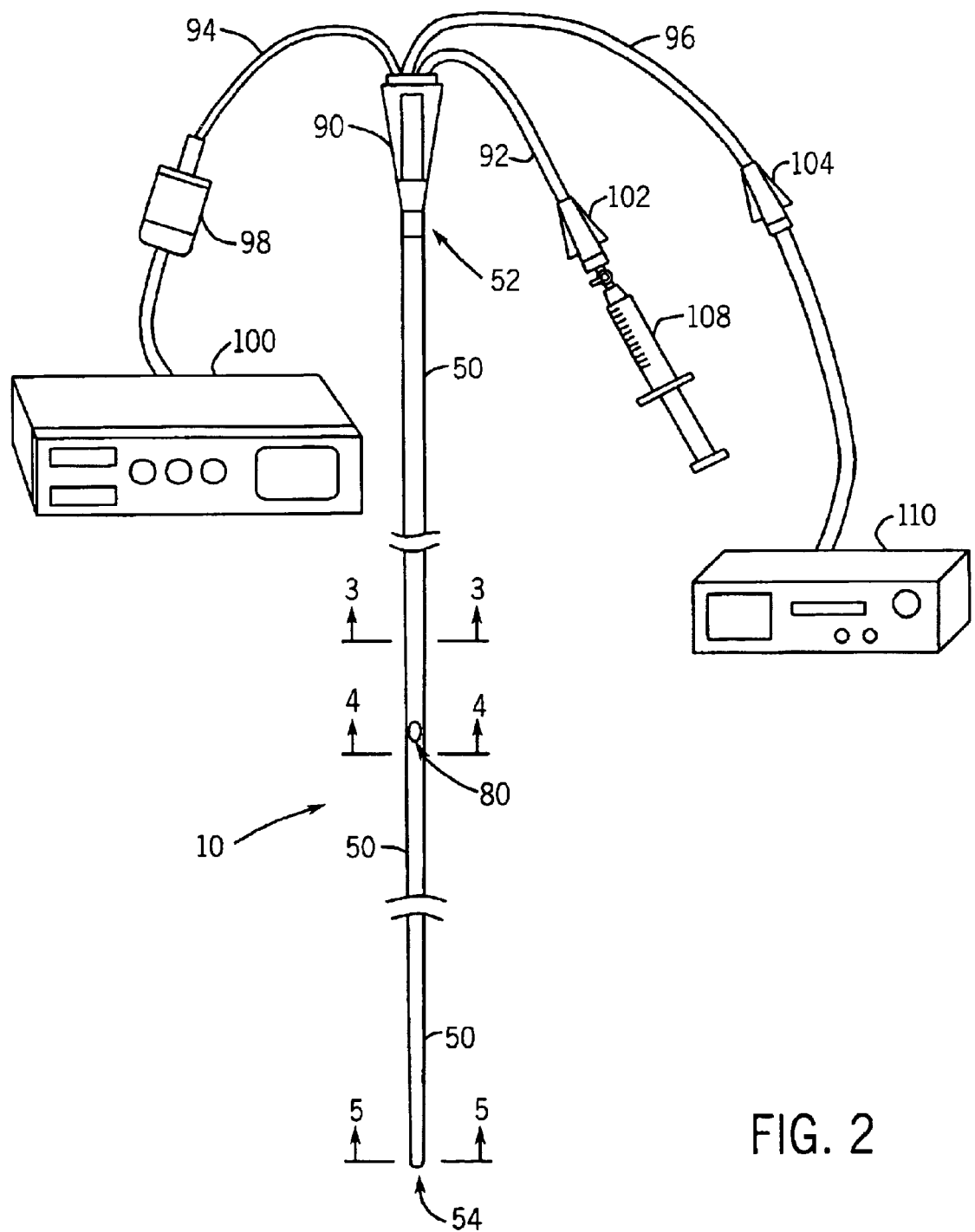
FIG. 2 is a pictorial view of the preferred embodiment of the peripheral catheter which employs the present invention.

The preferred embodiment of a peripherally inserted central catheter 10 is shown in FIG. 2 and includes a sheath 50 made of a polyurethane base polymer. It has a diameter of 5.0 to 5.3 French at its proximal end 52 and is tapered to a smaller diameter at its distal end 54. The sheath 50 is 55 cm in length and it has a radiopaque strip (not shown) along its entire length for visualization with x-ray imaging systems. Polyurethane offers many advantages over other materials for the sheath 50. Polyurethane is a more durable material enabling the use of thinner lumen walls. It offers less friction for ease of insertion; it is biocompatible; it has good tensile properties for safe insertion without kinks or fractures; it is resistant to hydrolysis, oxidation, oils and thermal degradation; it is thromboresistant and non-hemolytic; and it is rigid at room temperature but softer at body temperature to become more pliant, flexible and kink resistant when inserted into a vein. It also allows better transduction of pressures than other materials.

Figure 3:
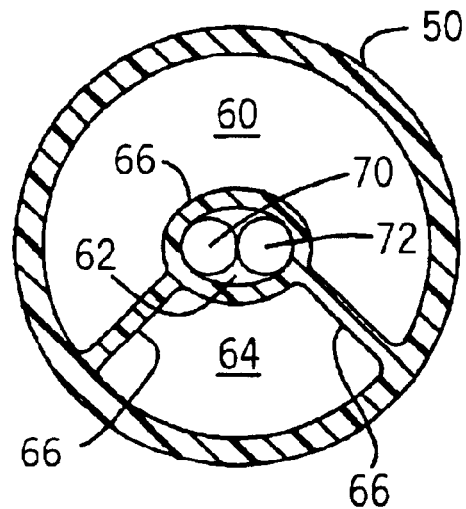
FIG. 3 is a cross-sectional view of the catheter along the plane indicated at 3 in FIG. 2.

Referring particularly to FIGS. 2 and 3, the first 30 cm of the catheter 10 as measured from its proximal end 52 encloses three lumens 60, 62 and 64. The lumens 60, 62 and 64 are formed by walls 66 integrally molded on the interior of the sheath 50. The lumen 62 is the smallest in size and it is substantially centered inside the sheath 50. It houses two optical fiber cables 70 and 72 which extend the entire length of the catheter 10 as will be described in more detail below. The wall 66 surrounding lumen 62 must be of sufficient thickness to protect the delicate optical fibers 70 and 72 and prevent them from kinking when the catheter is being inserted.

The lumen 64 is a 20 gauge lumen which also runs the entire length of the catheter 10, and as will be described below, it may be used for measuring blood pressure, drawing blood, infusing drugs, and guidewire housing during insertion of the catheter 10.

The lumen 60 is the largest lumen in the sheath 50. It is 17 gauge and it extends from the proximal end 52 of the sheath 50 to an opening, or port, 80 in the sheath 50 located 30 cm from the proximal end 52. It is thus located 25 cm from the distal end 54, and when the catheter 10 is fully inserted with its distal end 54 located in the superior vena cava 12, the port 80 is positioned within or proximal the subclavian vein 18. The large lumen 60 which the port 80 terminates thus provides a pathway for the infusion of fluids at a relatively high flow rate into the central venous system. Port 80 has a slit valve such as that disclosed in U.S. Pat. No. 5,810,789 and sold by CR Bard Inc. under the trademark "Groshong® valve". The Groshong® valve opens inward for blood aspiration and outward for infusion but remains closed when not in use. Because the valve remains closed when not in use, it seals the fluid inside the catheter and prevents it from coming in contact with the patient's blood. This closed ended system provided by the slit valve reduces the risk of blood reflux and air embolism. By maximizing the size of the lumen 60, increasing the size of the opening 80 and shortening the total length of the lumen 60 (i.e., 30 cm instead of 55 cm) a dramatic increase in fluid flow rate is achieved. In accordance with Poiseuille's Law:

$$Q = r^4 \Delta P / 8 \eta L$$

where:

Q=flow r=internal lumen radius

ΔP=change in pressure

L=lumen length

η=constant.

Figure 4:
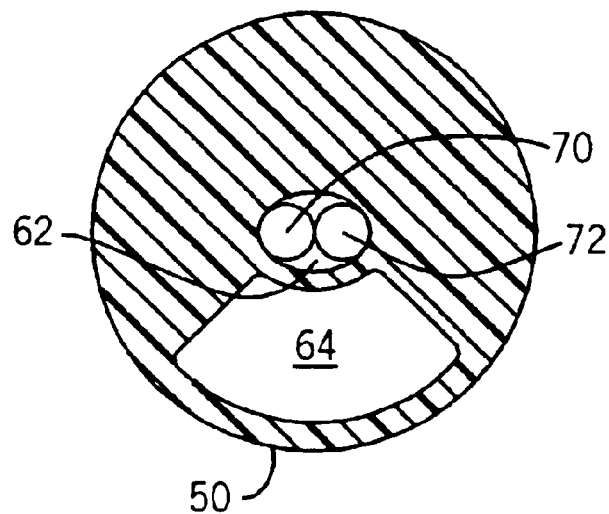
FIG. 4 is a cross-sectional view of the catheter along the plane indicated at 4 in FIG. 2.

Referring particularly to FIGS. 2 and 4, immediately distal the lumen opening 80 the internal configuration of the lumens housed by the sheath 50 changes. The lumen 60 is no longer present, but the lumens 62 and 64 continue on undisturbed. The outer diameter of the sheath 50 is also unchanged at this point, but it gradually decreases in size as one progresses toward the distal end 54.

Figure 5:
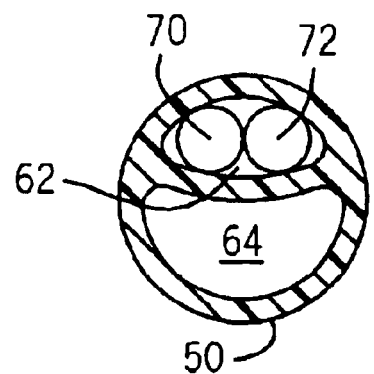
FIG. 5 is a cross-sectional view of the catheter along the plane indicated at 5 in FIG. 2.
Figure 6:
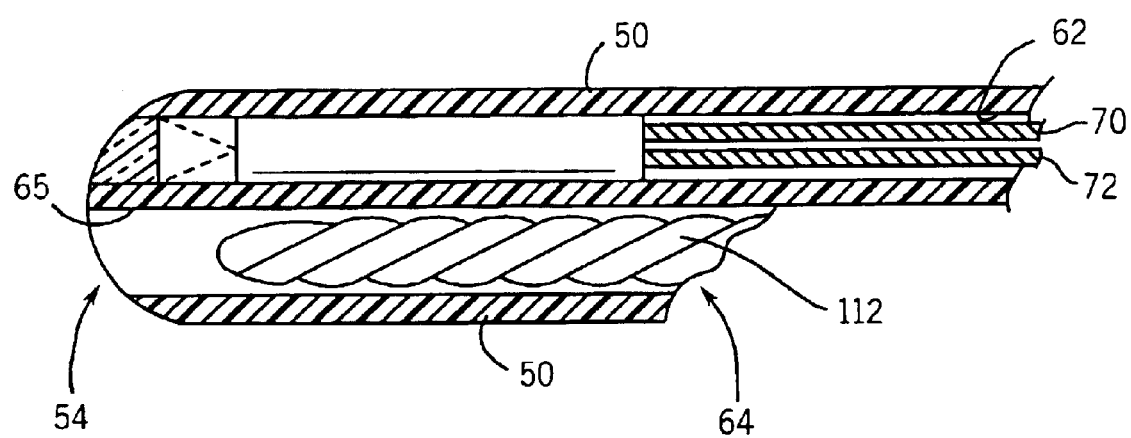
FIG. 6 is a partial view in cross-section of the distal end of the catheters of FIG. 2.

As shown best in FIGS. 2 and 5, at the distal end 54 of the sheath 50, the two lumens 62 and 64 terminate at openings in the tip of the catheter 10. The ends of the optical fiber cables 70 and 72 are exposed at the tip in a manner such as that disclosed in U.S. Pat. No. 5,196,004 so that light may be transported from the proximal end 52 in one optical fiber cable 70 to blood surrounding the catheter tip 54 and reflected light may be transported back to the proximal end 52 through the other optical fiber cable 72. As will be described below, this optical information is used to monitor central venous oxygen saturation. The lumen 64 extends through the distal end 54 and a port 65 is formed to communicate with surrounding blood as shown in FIG. 6. The outer diameter of the sheath 50 is reduced substantially at the distal end 54 to enhance the flexibility of the catheter and facilitate its insertion.

Referring particularly to FIG. 2, the three lumens 60, 62 and 64 are terminated at the proximal end 52 of the sheath 50 by a catheter manifold 90 such as that disclosed in U.S. Pat. No. 4,670,009 which is incorporated herein by reference. The catheter manifold 90 connects the lumens 60, 62 and 64 to respective catheter extension tubes 92, 94 and 96. The optical fiber cables 70 and 72 extend into the catheter extension tube 94 and terminate in a connector portion of a connector/receptacle 98 such as that described in U.S. Pat. No. 5,007,704 which is incorporated herein by reference. The receptacle portion of the connector/receptacle 98 forms part of an oxygen saturation measurement instrument 100 such as that described in U.S. Pat. No. 4,651,741 which is also incorporated herein by reference. The oxygen saturation instrument 100 measures oxygen saturation in blood flowing past the distal tip of the catheter 10 by detecting the relative reflectivity of the blood under red illumination and infrared illumination. The intensity signal $\lambda_1$ of red light reflected by blood back through optical fiber cable 72 is measured, as is the intensity signal $\lambda_2$ of the reflected infrared light. The intensity ratio $I=\lambda_2/\lambda_1$ is used to calculate oxygen saturation of the blood.

The catheter extension tubes 92 and 96 are terminated with connectors 102 and 104 which enable them to be connected to a number of different devices. Connector 102 is shown connected to a syringe 108. The syringe may be operated to infuse at a high flow rate a fluid through the large catheter lumen 60 to opening 80 aligned within or proximal to the subclavian vein 18. Such fluids might be, for example, resuscitation crystalloid, colloids, blood products or intravenous contrast.

The connector 104 is shown connected to a blood pressure monitor instrument 110. An instrument 110 such as that commercially available from Maxxim, Inc. under the trade name "CDXpress® transducer" may be used for this purpose. This is a continuous infusion transducer device in which a low constant flow of saline solution, or heparinized saline solution is pumped through the lumen 64 and out its distal opening at the tip of the catheter 10. A flow rate of 3 mL/hr is all that is required to flush the lumen 64 and insure that the blood pressure at the tip of the catheter 10 is accurately reflected through the lumen 64 to a pressure transducer (not shown) in the monitor 110.

Referring particularly to FIGS. 1 and 2, the catheter 10 is inserted in the patient through a peripheral vein in the arm (e.g., basilic, cephalic or cubital veins). A 1.88", 20 Gauge intravenous catheter is inserted in the peripheral vein and a 30 cm long, 0.018" diameter spring guidewire is passed through the intravenous catheter leading to the central venous system. The intravenous catheter is then removed and a 5.0–5.5 French sheath introducer and dilator unit (e.g., such as that sold by HDC Corporation under the trademark V=cath Safe-T-Peel"® or that sold by Cook Critical Care under the trademark Peel-Away Cook®) is inserted over the guidewire. The guidewire and dilator are removed leaving the introducer in the peripheral vein. The catheter 10 is then inserted through the introducer and guided into the central venous circulation terminating in the superior vena cava. As shown in FIG. 6, the catheter 10 is preloaded with a 0.025" diameter removable guidewire 112 that passes through connector 104, extension 96 and lumen 64 terminating proximal the catheter tip 54. The guidewire 112 provides increased catheter stiffness during the insertion process. The introducer sheath is split and peeled away from the catheter 10 once insertion is complete. Upon confirmation of catheter position with a chest X-ray, the preloaded removable guidewire 112 is withdraw and connector 104 is fastened to the pressure monitor 110. A securing device such as that sold by Arrow International under the trademark "Statlock®" may be used at the insertion site to prevent catheter dislodgement or migration.

When fully inserted the catheter 10 may be used to perform a number of functions. The central venous oxygen saturation ($S_{cv}O_2$) is monitored by instrument 100 and the venous blood pressure is monitored by instrument 110. Any fluids that need to be introduced into the central venous system may be injected using syringe 108 or an infusion pump (not shown in drawing). Because of its peripheral insertion, the catheter 10 may remain in place and fully functional for months.

It should be apparent that variations in the preferred embodiment described above are possible without departing from the spirit of the invention. For example, 55 cm is an optimal length for the peripheral catheter for insertion in the best peripheral veins in the upper arm, but lengths ranging from 35 cm to 65 cm are useful for peripheral insertion. Similarly, a range of sheath diameters are possible, but for peripheral insertion the diameter should not exceed 5.5 French. Also, other devices can be connected to and use the two lumens 60 and 64. For example, infusion pumps, radiocontrast power injectors, and pressure bags for lumen 60 and syringes or infusion pumps for lumen 64. Also, while in most procedures it is sufficient to extend the distal tip of the catheter into the superior vena cava, it will be understood by those skilled in the art that the catheter tip may also be extended into the right atrium of the patient's heart. Structurally, no changes in the catheter are required to do this, although another 5 to 10 cm of length may be helpful.

What is claimed is:

1. A peripherally inserted central venous system catheter which comprises:

a sheath having a length and a diameter suitable for extending from a peripheral vein insertion point on a patent to the superior vena cava of the patient, the sheath being constructed of a material suitable for insertion into the venous system of a subject through a peripheral vein and forming two lumens therein which extend from its proximal end at the insertion point to its distal end in the superior vena cava;

a pair of optical fiber cables disposed in one of the lumens and extending from the distal end to the proximal end of the sheath;

a connector fastened to the proximal ends of the two optical fiber cables for connecting them to an oxygen saturation measurement instrument; and a second connector fastened to the proximal end of the other of said two lumens for connecting the second lumen to a medical instrument, wherein central venous oxygen saturation of the patient's blood is measured and a medical procedure is simultaneously performed using the medical instrument.

2. The catheter of claim 1 in which the medical instrument is a blood pressure monitor which measures blood pressure at the distal end of the sheath.

3. The catheter as recited in claim 1 in which the sheath has a length greater than 35 cm.

4. The catheter as recited in claim 3 in which the sheath has a diameter less than 5.5 French.

5. The catheter as recited in claim 1 in which the sheath is formed from a polyurethane base polymer.

6. A peripherally inserted central venous system catheter which comprises:

a sheath having a length and a diameter suitable for extending from a peripheral vein insertion point on a patent to the superior vena cava of the patient, the sheath being constructed of a material suitable for insertion into the venous system of a subject through a peripheral vein and forming two lumens therein which extend from its proximal end at the insertion point to its distal end in the superior vena cava;

a pair of optical fiber cables disposed in one of the lumens and extending from the distal end to the proximal end of the sheath;

a connector fastened to the proximal ends of the two optical fiber cables for connecting them to an oxygen saturation measurement instrument; and a second connector fastened to the proximal end of the other of said two lumens for connecting the second lumen to a medical instrument, wherein central venous oxygen saturation of the patient's blood is measured and a medical procedure is simultaneously performed using the medical instrument; and in which a third lumen is formed in the sheath and extends from its proximal end to a point intermediate the ends of the sheath where it communicates with blood surrounding the sheath through a port formed in the sheath; and a third connector is fastened to the proximal end of the third lumen for connecting the third lumen to a fluid infusion device;

wherein the third lumen is larger than said two lumens such that fluids may be infused into the central venous system of the patient through said port.

7. The catheter of claim 6 in which the medical instrument is a blood pressure monitor which measures blood pressure at the distal end of the sheath.

8. The catheter as recited in claim 6 in which the sheath has a length greater than 35 cm.

9. The catheter as recited in claim 8 in which the sheath has a diameter less than 5.5 French.

10. The catheter as recited in claim 6 in which the sheath is formed from a polyurethane base polymer.

* * * * *